United States Patent [19]

Hachey

[11] Patent Number: 5,130,639
[45] Date of Patent: Jul. 14, 1992

[54] APPARATUS FOR PARTICLE DETERMINATION IN LIQUID METALS

[75] Inventor: Raynald Hachey, Shipshaw, Canada

[73] Assignee: Alcan International Limited, Montreal, Canada

[21] Appl. No.: 525,135

[22] Filed: May 17, 1990

[30] Foreign Application Priority Data

May 18, 1989 [CA] Canada .................................. 600148

[51] Int. Cl.⁵ .................................................. G01N 27/00
[52] U.S. Cl. .................................. 324/71.4; 324/71.1; 324/444
[58] Field of Search ...................... 324/71.1, 71.4, 720, 324/444, 442, 613

[56] References Cited

U.S. PATENT DOCUMENTS

| | | | |
|---|---|---|---|
| 3,944,917 | 3/1976 | Hogg et al. | 324/71.1 |
| 4,060,717 | 11/1977 | Sitek | 324/71.1 X |
| 4,435,681 | 3/1984 | Masuda et al. | 324/71.1 X |
| 4,527,114 | 7/1985 | Coulter | 324/71.1 |
| 4,555,662 | 11/1985 | Doutre et al. | 324/71.4 |
| 4,600,880 | 7/1986 | Doutre et al. | 324/71.1 |
| 4,843,325 | 6/1989 | McKee, Jr. | 324/439 |
| 4,972,137 | 11/1990 | Dunstan et al. | 324/71.4 |
| 5,025,220 | 6/1991 | Colvin et al. | 324/444 X |
| 5,039,935 | 8/1991 | Hachey et al. | 324/71.4 |

Primary Examiner—Kenneth A. Wieder
Attorney, Agent, or Firm—Cooper & Dunham

[57] ABSTRACT

In an apparatus for on-line particle determination in molten metals, a sample of molten metal is drawn through a calibrated passage while a steady current is established through the passage between two electrodes on opposite sides thereof. Particles moving through the passage produce voltage pulses whose magnitude and rate indicate respectively their size and number per unit volume. The wanted test signal can be obtained between the two current carrying electrodes, or between two other electrodes disposed on opposite sides of the passage. The electrodes form an interference-receiving antenna so that the wanted low signal/noise ratio test signal is overlaid with interference from neighboring sources. This interference is reduced by a cancellation signal produced by a cancellation antenna constituted by a similar pair of electrodes, either separate from the main current-carrying electrodes or having one of them in common. A four electrode configuration permits the diameter of the passage to be monitored continuously. A five electrode configuration has three electrodes separate from the current-carrying electrodes forming the two antennae and connected differentially. A further electrode if provided is used to minimize ground loops in the signal path. A head member carrying the tube and electrode cluster is mounted to move between operative and storage positions relative to a main body member carrying the power supply; these are made symmetrical about a longitudinal axis so that interference signals are in anti-phase and cancel.

35 Claims, 11 Drawing Sheets

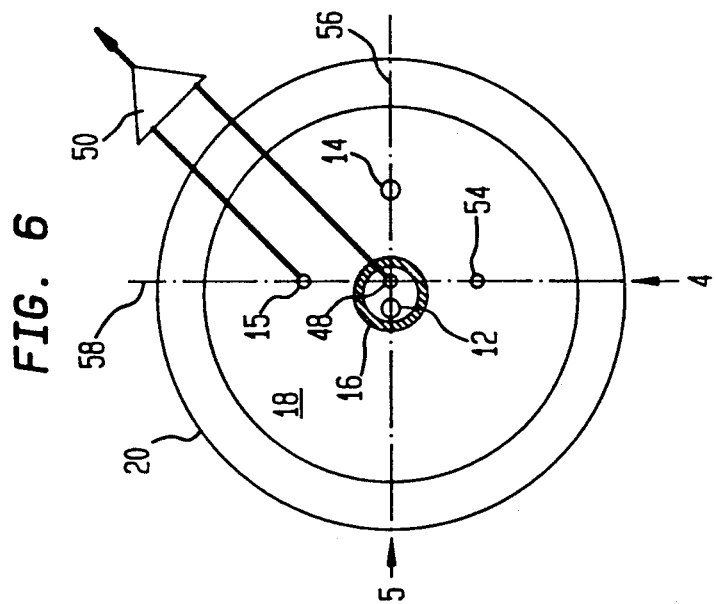
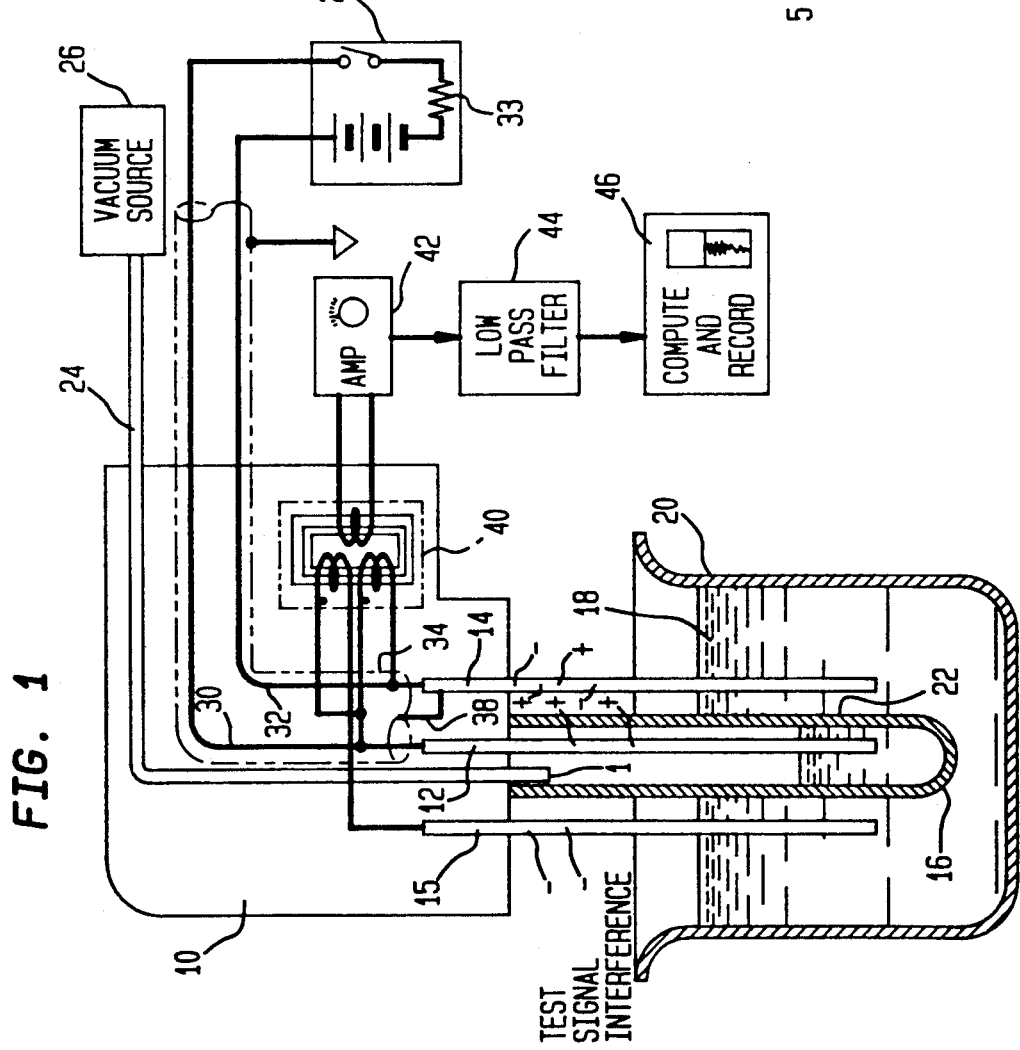

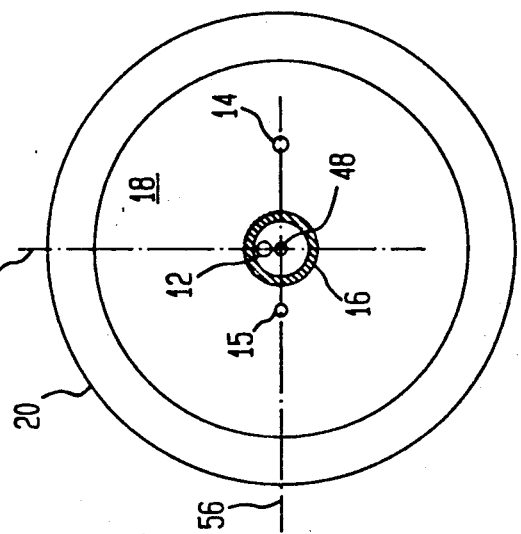
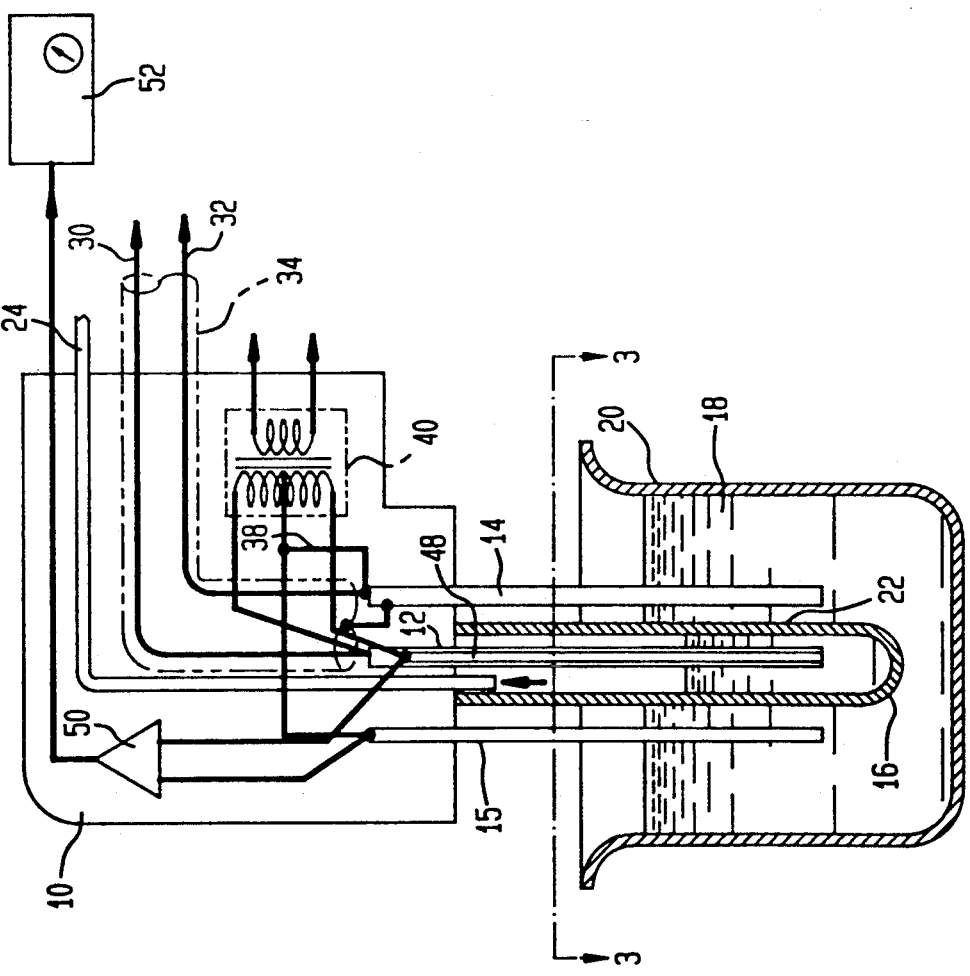

APPARATUS FOR PARTICLE DETERMINATION IN LIQUID METALS

FIELD OF THE INVENTION

This invention is concerned with improvements in or relating to apparatus for particle determination in liquid metals, namely for the detection and measurement of the number and/or size of particles present in liquid metals.

REVIEW OF THE PRIOR ART

There are disclosed and claimed in U.S. Pat. Nos. 4,555,662 and 4,600,880 a method and apparatus for the on-line detection of the number and size of solid particles in liquid metals, particularly liquid aluminum. The apparatus which has been developed is known as the "LiMCA" analyser, and briefly comprises a vessel of suitable heat-resistant, electrically non-conductive material having a small, precisely-dimensioned passage in a side wall. The vessel is immersed in the liquid metal to be tested and a uniform stream thereof is passed through the passage, usually by means of a vacuum drawn in the vessel interior, while a substantially constant electric current is established through the stream between two electrodes disposed respectively inside and outside the vessel. The particles of interest are usually non-conductive and the passage of a particle through the bore is accompanied by a change in the electrical resistance through the bore to produce a pulse whose amplitude is an indication of the size of the particle. The number of pulses produced while a fixed volume of metal passes through the bore is an indication of the number of particles per unit volume in the metal.

The bore cannot be too small, or it is easily blocked by the larger particles, and small particles passing through a large bore will produce pulses of indeterminate shape and of magnitude little different from that of the background random "noise" signals. It is found in practice difficult to extract the wanted pulse signals reliably from these noise signals, since unless considerable care is taken they may be of about the same order of magnitude as the wanted signals for the smaller particles. To this end the supply current must be carefully filtered and smoothed, the vacuum (or pressure) used to move the metal through the bore must be free of pump-generated pulses, and the entire apparatus must be shielded as much as possible against outside electromagnetic interference. Many types of equipment that inevitably are present in an industrial environment may be sources of such interference, such as electric motors, electric welding machines, fluorescent lights, high voltage lines and induction furnaces, the interference either being propagated through the power supply cables, or by radiation through space.

The design and use of filters to reduce or eliminate interference is now a well-developed art, but with this apparatus is made difficult by the relatively low voltage signals characteristic of the particle-indicating pulses (e.g. about 2-1000 microvolts peak), and the fact that the pulse frequencies (corresponding to the number of particles per unit time passing through the passage) are in the range 150-10,000 Hertz, which is of the same order as those of many of the interfering noise pulses. Shielding can be provided to reflect or absorb the broadcast radiation before it reaches the apparatus, but it is impossible to achieve the ideal shield, consisting of an entirely closed metal box, because of the need for inputs and outputs to and from the box interior; the input and output cables must therefore also be fully shielded, so that effectively they become an extension of the closed box interior. A technique found to be of value is to isolate parts of the test circuit from one another, whenever that is possible, to avoid the formation of local current loops that are particularly receptive of such interference, either by the use of known opto-insulators or with the help of insulation transformers.

A particularly difficult source of interference to deal with is an induction furnace, in that it broadcasts punctual and continuous bursts of strong interference that are particularly easily confused with the required signals, while filters, shields and insulation have limited efficiency in the case of such a source. It is one of the principal virtues of the "Limca" apparatus that it can be used for "on-line" tests to give results in seconds, compared to prior apparatus which required several hours or even days, but this does dictate that the apparatus is close to the liquid metal source, with the above-described problems if this is an induction furnace.

DEFINITION OF THE INVENTION

It is therefore an object of the invention to provide in such apparatus means for producing an interference cancellation signal that can be used to correct the wanted test signal by reduction of as much as possible of the interfering component or components thereof.

It is another object to provide apparatus in which such an interference cancellation signal can be produced and used to correct the wanted signal prior to any amplification of the wanted signal.

It is a further object to provide a new apparatus in which provision is made for monitoring the size of the passage in order to evaluate and correct for the effect of change of its size on the test signal.

It is a further object to provide a new apparatus that is compact and facilitates reduction by avoidance and cancellation of unwanted interference signals, while also being more easily transportable and usable for "on-line" determinations.

Apparatus in all aspects of the present invention for the detection and measurement of particles in liquid metal comprises:
- electrically insulating wall means having a passage therein for the passage of molten metal therethrough;
- means for passing molten metal through the passage in the form of a stream thereof;
- a pair of current supply electrodes disposed on opposite sides of the wall means for insertion into the liquid metal to establish a current path between them through the passage; and
- current supply lead means connected respectively to the current supply electrodes for passing a current in the current path from a source thereof.

Apparatus in accordance with the invention from a first aspect comprises:
- at least a third electrode for insertion into the liquid metal with the first-mentioned pair of electrodes;
- test lead means connected to a pair of the electrodes on opposite sides of the wall means for connection to detection means for detecting the voltage difference between the pair of electrodes resulting from the current and for detecting changes in the voltage difference resulting from the passage of differently-conducting particles through the passage and for the consequent production of a corresponding test signal;

the last-mentioned pair of the electrodes constituting at least part of an interference antenna producing an interference signal from incident electric or magnetic interference, which interference signal is superimposed on the test signal;

another pair of the three electrodes constituting a cancellation antenna disposed adjacent the said interference antenna to produce an interference cancellation signal from the said incident interference;

and means for adding the interference cancellation signal to the said test signal in opposition to the interference signal to at least reduce the amplitude of the interference signal.

Apparatus in accordance with the invention from another aspect comprises:

third, fourth and fifth electrodes for insertion into the liquid metal with the pair of current supply electrodes;

test lead means connected to a first pair of the third, fourth and fifth electrodes on opposite sides of the wall means and for connection to detection means for detecting the voltage difference between the first pair of electrodes resulting from the current in the current path for detecting changes in the voltage difference resulting from the passage of differently-conducting particles through the passage, and for the consequent production of a corresponding test signal;

the first pair of the third, fourth and fifth electrodes constituting at least part of an interference antenna producing an interference signal from incident electric or magnetic interference, which interference signal is superimposed on the test signal;

a second pair of the third, fourth and fifth electrodes constituting a cancellation antenna disposed adjacent the said interference antenna to produce an interference cancellation signal from the said incident interference;

and means for adding the interference cancellation signal to the test signal in opposition to the interference signal to at least reduce the amplitude of the interference signal.

Apparatus in accordance with the invention from a further aspect comprises:

a third and fourth electrode for insertion into the liquid metal with the pair of current supply electrodes so as to be disposed on opposite sides of the wall means from one another;

test lead means connected respectively to the pair of third and fourth electrodes for connection to measuring means for detecting the voltage difference between those electrodes and changes in the voltage difference resulting from the passage and changes in the voltage difference resulting from the passage of differently-conducting particles through the passage and for the consequent production of a corresponding test signal;

and measuring means connected to the test lead means to receive the test signal that is thereby produced.

Apparatus in accordance with the invention from a further aspect comprises:

test lead means connected to a pair of electrodes on opposite sides of the wall means from one another and for connection to means for detecting changes in the voltage difference between them resulting from the passage of differently-conducting particles through the passage and in the test signal that is thereby produced;

a third and a fourth electrode for insertion into the liquid metal with the said pair of electrodes and also disposed on opposite sides of the wall means;

and measuring means connected between the third and fourth electrodes for determination of the size of the passage by determination of the voltage difference therethrough produced by the electric field in the current path.

Preferably apparatus in accordance with the invention in any of its aspects includes an additional electrode for insertion into the liquid metal, and means connecting this additional electrode in the apparatus to minimize ground loop current paths in the test signal path; it may also be used to reference the power supply to reduce spurious AC current signals.

Preferably also each electrode comprises an immersible portion of tungsten and a mounting portion of a metal having a contact potential of less than 1 millivolt with tungsten at the temperature of operation. Apparatus in accordance with the invention from a further aspect comprises an apparatus body mounting the electrically insulating, wall means and the electrodes which is symmetrical about a longitudinal plane, and at least a power supply for the apparatus is in two mirror symmetrical portions disposed on opposite sides of the longitudinal plane.

Apparatus in accordance with the invention from a further aspect comprises a head member mounting the electrically insulating wall means and the electrodes;

a body member mounting at least a power supply for the apparatus; and arm means mounting the head member for movement relative to the body member between an operative position in which the electrodes are insertable in the molten metal and a storage position in which they are spaced from the molten metal.

DESCRIPTION OF THE DRAWINGS

Particular preferred embodiments of the invention will now be described, by way of example, with reference to the accompanying diagrammatic drawings, wherein:

FIG. 1 is a combined schematic side elevation of the head portion of a first, three-electrode embodiment, together with a block diagram of the operating circuit;

FIG. 2 is a schematic side elevation of the head portion only of a second, four-electrode embodiment;

FIG. 3 is a cross-section in plan of the second embodiment, taken on the line 3—3 in FIG. 2;

FIG. 6 is a cross-section in plan of the embodiment of FIGS. 4 and 5, taken on the line 6—6 in FIG. 5.

DESCRIPTION OF THE PREFERRED EMBODIMENTS

Figure 5:
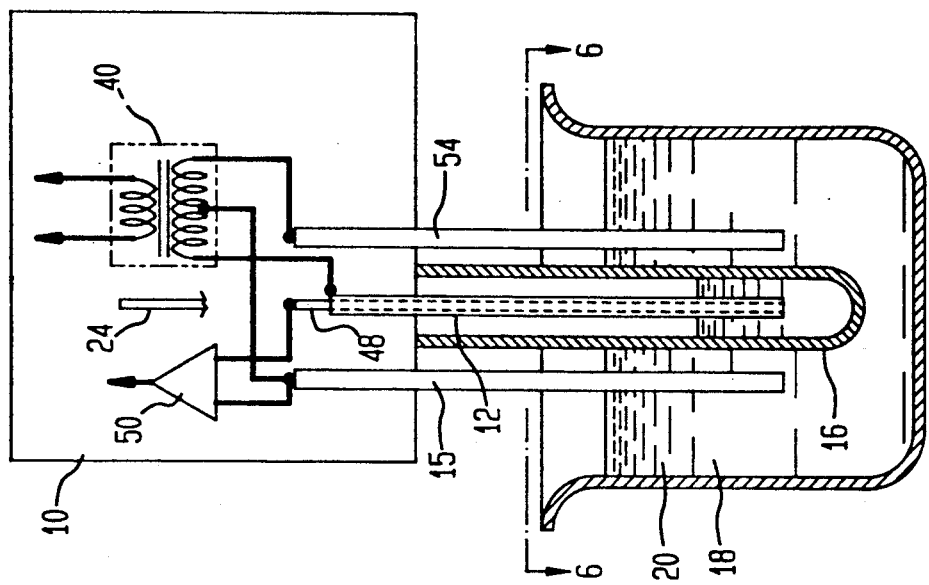
FIG. 5 is an end elevation of the embodiment of FIG. 4, taken in the direction of the arrow 5 in FIG. 6.

The invention in a first aspect, as illustrated by FIG. 1, is applied to a "LiMCA" (trade name) sampling head 10 comprising three transversely-spaced parallel downwardly-protruding electrodes 12, 14 and 15, the electrode 12 extending into a sampling tube 16, while the electrodes 14 and 15 extend directly into the molten metal 18 to be examined, which is shown for convenience in illustration as contained in a vessel 20. However, in all of the embodiments of the invention any body of molten metal can be tested, such as a flowing stream passing in a transfer trough, and it is one of the advantages of apparatus of the invention that it can rapidly produce useful readings while the metal is flowing. In this embodiment the electrodes 12 and 14 are current-carrying, the electrode 12 being positive and the electrode 14 negative, but the apparatus is not polarity sensitive and in other embodiments their polarities may be reversed.

The tube 16 is provided in the portion of its side wall between the two current-carrying electrodes 12 and 14 with an accurately-formed borehole or passage 22, through which metal is drawn into the cell formed by the tube by a vacuum established in the cell via an outlet tube 24 by a vacuum source 26, while a relatively heavy constant direct current, usually of the order of 6–60 amps, is fed to the electrodes 12 and 14 from a D.C. current source 28, usually a heavy-duty rechargeable D.C. battery, via current-carrying leads 30 and 32. The power source includes a ballast resistor 33 which reduces the voltage supplied to the electrodes from about 6 volts to about 0.6 volt, while at the same time stabilizing its value by a corresponding factor. The two leads 30, 32 are enclosed in a shield 34 to reduce pick-up, the shield and the remainder of the circuit being connected to a common ground and also being electrically connected by connection 38 to the electrode 14 for it to serve as a ground reference electrode. The signal consisting of the resultant, wanted, test, pulse-containing voltage difference detected between the electrodes 12 and 14 is fed in this embodiment to a differential preamplifier circuit 40 comprising also a high pass filter (150 Hz).

Although in all these embodiments the test is carried out while the molten metal is drawn into the tube by a vacuum, it is also possible to test while the metal is expelled from the tube by an internally applied pressure; if testing is carried out during both entry and exit of the metal the two results that are obtained can be averaged.

Although the cables 30 and 32 are shielded as effectively as is possible, and for as much of their length as is possible, the electrodes 12 and 14 form what is defined herein for convenience in terminology as an interference antenna, the effectiveness of which as an antenna cannot easily be reduced without impairing the ease of installation, use and mobility of the measuring head and its connecting cables. This interference antenna inevitably picks up extraneous signals from local sources of noise and, because of the difficulty, if not impossibility, of shielding the two electrodes 12 and 14, it is quite efficient as such. In a particular embodiment the electrodes 12 and 14 can measure up to 90 cms (36 ins) in length, are spaced apart about 5 cms (2 ins) and are immersed up to 15 cms (6 inches) in the molten metal to result in an electrode loop antenna of effective cross-section about 387 sq. cm. (60 sq.in.). This loop antenna is found to be quite highly directional, to the extent that it can even be used to detect the direction of the source or sources of the incident interference.

As discussed above, one of the most difficult interfering sources to deal with is an induction furnace in that it broadcasts its interference in or near to the sampling frequency range characteristic of this apparatus (i.e. 200 Hz to 10 kHz), so that it cannot be rejected by a passband or notch filter without adversely affecting the wanted signals. As explained above, a major advantage of this type of apparatus is the ability to use it "on-line", which usually requires its use close to the induction furnace, e.g. within about 15 meters (45 feet), where it is well within the broadcast area of the interference. Shields and insulation are of limited efficiency in the presence of such interference and so close to its source, and a signal pre-amplifier cannot be located to receive the wanted signals without also receiving the unwanted signals.

In accordance with an aspect of the invention, in this first three-electrode embodiment, an additional or supplementary signal cancellation loop antenna is provided, formed by the combination of the electrode 12 and the third electrode 15, the latter also extending downward from the head directly into the melt so as to lie in the same plane as the electrodes 12 and 14. The electrode 15 is disposed on the opposite side of electrode 12 from electrode 14 and is equally spaced from the electrode 12, so that the resultant cancellation loop antenna is of the same effective cross-section area as the interference antenna, which areas will always remain equal despite any movements of the head and the differences in the depth of immersion of the three electrodes in the melt, the melt acting as a short circuit so that the area decreases as the depth of immersion increases. This third electrode will be long enough to always have its lower end insertable in the metal during a test procedure, and conveniently is of the same length as the two electrodes 12 and 14, but does not need to be as thick, since it carries only the small signal currents. Because of their physical disposition with the positive electrode 12 in common the interference signals in the interference and cancellation antennae are automatically exactly out of phase.

As illustrated the differential amplifier that is employed in the pre-amplifier/filter 40 is a current transformer, the signal from the interference antenna 12, 14 being fed across one primary winding, while the signal from the cancellation antenna 12, 15 is fed across the other winding. It will be seen therefore that the interference cancellation signal from the antenna 12, 15 is used to cancel any interference signal from antenna 12, 14 prior to any amplification of either signal; this has the advantage of minimizing problems caused by noise and phase and/or gain changes that would be produced by any intervening amplifier or amplifiers prior to sequel combination. The pre-amplifier is of a type providing the maximum available gain (e.g. up to about 100×), since such a static device introduces less noise into the signal than the usual equivalent electronic devices. It is not however essential that a differential pre-amplifier be employed and other arrangements are described below. If an electronic type amplifier is used then preferably it is supplied with its operating power from a separate small D.C. battery to reduce the possibility of unwanted signal pick-up from a mains-operated power supply. Such a transformer differential amplifier also preferably is of the type employing split balanced windings to provide automatic cancellation of the interference signals that are produced therein. With such a system particular care must be taken to reduce as much as possible any ground loop voltages that may be generated, since they are also fully amplified by the amplifier or amplifiers which follow it, and arrangements to that end will be described below.

The output of pre-amplifier/filter 40 is fed to a variable gain amplifier 42 used to adjust the signal level obtained, the output of which is in turn fed to a low pass filter 44 which, together with the high pass filter in pre-amplifier/filter 40, completes a passband filter in the range 150 to 10,000 Hertz, the output of the filter 44 being fed to a computation and recording apparatus 46, as described in detail in the said U.S. Pat. Nos. 4,555,662 and 4,600,880, the disclosures of which are incorporated herein by this reference. This recording apparatus produces a permanent visible record indicating the number of particles per unit volume of metal, their individual size if required, and their relative size distribution.

In another three-electrode embodiment which is not illustrated the current carrying cables 30 and 32 are connected between the two electrodes 12 and 15, while the differential amplifier 40 remains connected as before. However, with such a connection not only is it no longer possible to reduce ground loop voltages, but any present are strongly amplified by the following amplifier.

FIGS. 2 and 3 illustrate a second embodiment employing a four electrode head which not only provides the advantages of the three electrode head described above, but also permits in addition constant measurement of the transverse size (transverse dimensions, equivalent or effective diameter, or cross-sectional area) of the passage 22. It must be understood that the conditions of operation of the apparatus are unusually severe because of its use with molten metal. It is desired to detect and measure particles in the molten metal of as small as 10 microns equivalent diameter, and the usual equivalent diameter for the passage 22 is 300 microns, which can be formed to a tolerance of ±2 microns. The value of the equivalent diameter is usually quoted since the passage is unlikely to be truly circular, at least within the obtainable tolerances at the start, and may wear unevenly in use to become even less truly circular. This extremely small diameter passage is subjected periodically to an intense flow of molten metal, which in the case of aluminum and its alloys is at temperatures of 700°-800° C., while carrying the relatively high current of about 6-60 amps. The resistance through the passage is only of the order of 2 milliohm, but with the high currents employed even this small resistance will produce significant heating in the passage. The molten metal has a corrosive action toward the material of the tube 16, especially some alloys, such as those of high magnesium content, and this is increased by the scouring effect of the metal being forced rapidly through the passage, with the result that in use it increases in cross-section area.

With a potential difference between the electrodes 12 and 14 of about 0.6 volts the potential difference across the passage 22 is about 120 millivolts, while the signal produced by the passage of a 10 micron diameter particle is only of the order of microvolts, which in practice is already at the threshold of detectability among the noise and interference. An increase in cross-section area of the passage results in a two power decrease in its resistance, and therefore a four power decrease in the signal produced by a particle passing through it, so that the particles will be measured by the apparatus as being of smaller diameter. An increase in the supply voltage would increase the signal level, but also increases the power requirements which are already unusually high for a test apparatus. The passage cannot in practice be made initially much smaller in diameter without the danger that it will become blocked by a large agglomerated particle, and it is therefore important that it not get any larger, or at least that if it does the operator is aware of this and can apply a correcting factor to the signals. It is also important that the operator can readily detect "on line" when the passage has become too large for a useful signal to be obtained and the tube 16 must be replaced.

FIG. 2 shows the head 10 schematically in side elevation, while FIG. 3 shows it in section taken on the line 3—3 in FIG. 2 so that the relative location of the four electrodes can be seen. The fourth auxiliary electrode 48 also does not carry the test current from cables 30 and 32, and can also be of small diameter, as with the auxiliary electrode 15. This fourth electrode 48 is disposed inside the tube 16 so that the three electrodes 14, 15 and 48 lie in the same plane 56. The two test current-carrying electrodes 12 and 14 form the interference antenna and are connected to one half of the input winding of differential transformer amplifier 40, while the two non-current-carrying electrodes 15 and 48 form the cancellation antenna and are connected to the other half of the transformer input winding, the connections being appropriate to obtain the necessary cancellation. In this embodiment the interference and cancellation antennae are not exactly co-planar, the electrodes 48 and 12 being placed as closely together as possible and in a plane 58 at right angles to the plane 56.

In addition the electrodes 15 and 48 are connected to the input of a high input impedance amplifier 50 measuring the voltage difference between them, and feeding this measurement to a computer circuit 52 which employs it to determine the size of the passage 22, the voltage difference of course decreasing as the hole increases in size and its effective resistance decreases.

Such measurement is possible between these two auxiliary electrodes, which do not themselves carry any of the test current, since the large test current between the two electrodes 12 and 14 creates an electric field in the pool of molten metal and through the borehole 22. In any resistance path between any two electrodes on opposite sides of the hole the resistance of the metal in the bath 18 and in the tube 16 is so low compared to that through the narrow borehole that the resistance in that path is essentially that through the borehole alone, and upon insertion of any two other electrodes in this electric field the potential difference between them can be measured by a voltmeter of adequate sensitivity and high imput impedance, such as an electronic voltmeter. The use of such an instrument also permits the resistance of the auxiliary electrodes themselves to be ignored. The remainder of the utilisation circuit is as illustrated in FIG. 1.

It will also be seen that it is possible with such a four electrode configuration to measure the test signal between the two auxiliary electrodes 15 and 48, since they are on opposite sides of the borehole, and the potential difference between them will vary with the resistance in the current path between the two current-carrying electrodes 12 and 14.

Figure 4:
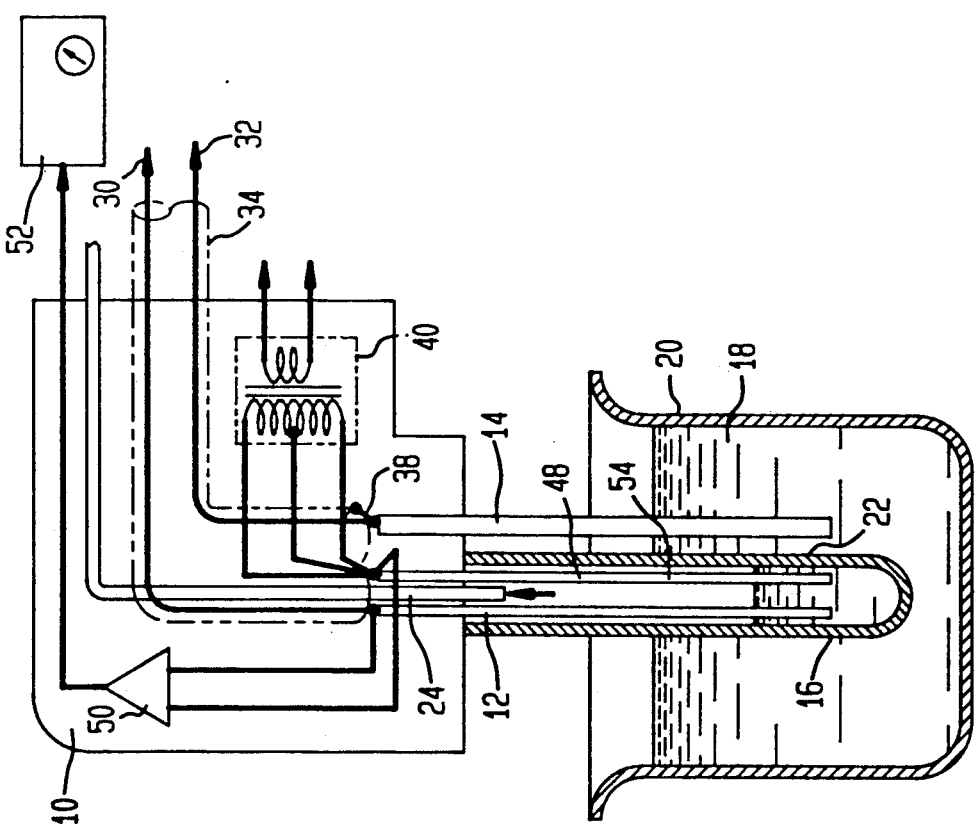
FIG. 4 is a schematic side elevation of the head portion only of a third, five-electrode embodiment, taken in the direction of the arrow 4 in FIG. 6.

FIGS. 4 through 6 illustrate a third embodiment employing five electrodes 12, 14, 15, 48 and 54, which provides for automatic equalization of the interference and interference cancellation signals and measurement of the passage effective diameter, together with reduction of ground loops and their respective unwanted voltages. Thus, the two electrodes 12 and 48 are disposed together in the tube 16, while the electrode 15 and a fifth electrode 54 are disposed on opposite sides of the electrode 48, with all of their longitudinal axes parallel. The axes of the three electrodes 15, 48 and 54 all lie in the same vertical plane, the electrodes 15 and 48 constituting one antenna and the electrodes 48 and 54 the other antenna, the transverse spacing between the two electrodes 15 and 48 being the same as that between the two electrodes 48 and 54, so that the corresponding opposing antennae have substantially equal areas. Either antennae can constitute the interference antenna or the cancellation antenna, as will be explained below.

As before, the power cables 30 and 32 are connected between the two heavy current-carrying electrodes 12 and 14 so that these generate an electric field in the resistance path that they establish in the metal pool through the passage 22, while the wanted test signal is measured between an associated pair of the auxiliary electrodes. In the embodiment illustrated the test signal is obtained between the electrodes 48 and 54, which therefore also constitute the interference loop antenna; they are connected at opposite ends of the input winding of the current transformer differential amplifier 40 to maximize the available test signal. The electrodes 48 and 15 constitute the cancellation loop antenna and are connected between the respective end and the centre tap of the input winding.

The amplifier 50 is also connected between the two electrodes 15 and 48, but could equally well be connected between the two electrodes 48 and 54, to measure the voltage difference and thus monitor the passage size. Since the electrodes 12 and 14 still form an effective loop antenna they are mounted in the head so that their plane 56 (FIG. 6) is at right angles to plane 58 of the three electrodes 15, 48 and 54, so that there will be a minimum of interference pick-up between the two antenna systems. By using three signal electrodes that do not need to carry the heavy test current it is possible to provide between the central electrode and a junction between the other two electrodes a "virtual" central reference that is as free as it is possible to get of unwanted interference pick-up; it is then possible to use at this reference location to amplify the wanted signal an electronic pre-amplifier, such as a relatively inexpensive and stable high input impedance battery-operated instrument amplifier.

In all of the embodiments described one of the electrodes must be used to reference the power supplies if they are A.C. operated, in order to minimize ground loops in the wanted signal path. The use of an additional electrode specially for this purpose is described below, but in the absence of such a special electrode it is usual to employ the current-carrying electrode outside the tube 16 (the electrode 14 in these embodiments) for this purpose.

Figure 7:
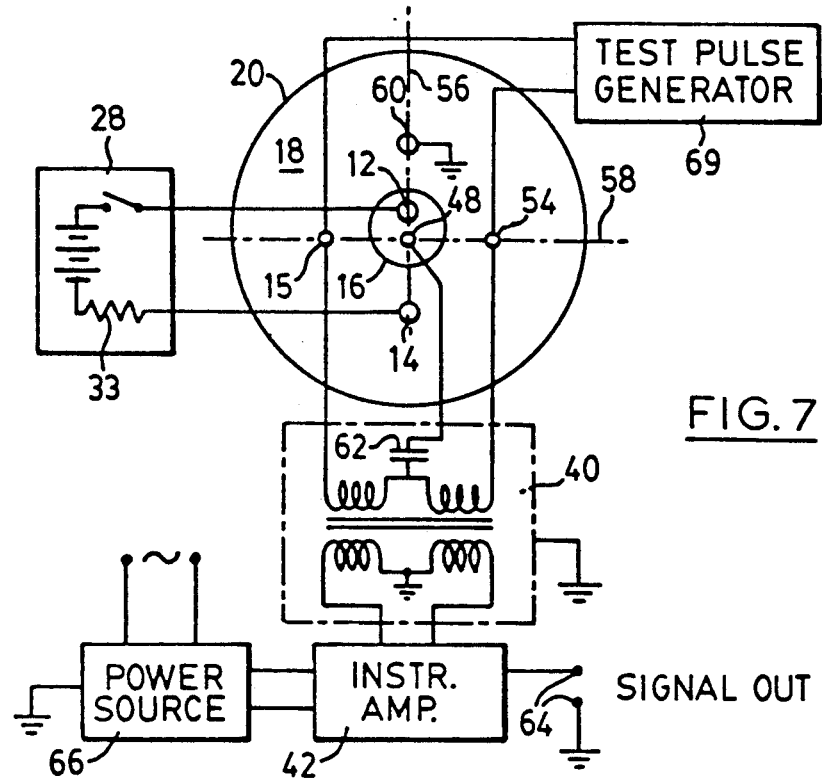
FIG. 7 is a cross-section in plan similar to FIG. 6, together with a schematic circuit diagram, of a further six-electrode embodiment.

FIG. 7 illustrates another circuit for the apparatus employing a "virtual" central reference as with the circuit of FIG. 6, and also employing a further electrode 60 for use as a reference for the power supplies, this further electrode being disposed at any convenient location outside the tube, preferably in the same plane 56 as the electrodes 12, 14 and 48, so as again to be in a plane perpendicular to that of the signal measuring electrodes 15, 48 and 54. Such a further electrode employed solely for this reference purpose can also be provided with the other embodiments and constitutes a fourth electrode in the embodiment of FIG. 1, a fifth electrode in the embodiment of FIGS. 2 and 3, and a sixth electrode in the embodiment of FIGS. 4–6. This avoids the need to use one of the current-carrying electrodes for this purpose, which can introduce ground loop pulses into the circuit as particles pass through the bore.

The same references as are used in FIGS. 1 to 6 are used in FIG. 7 for equivalent circuit elements. The electrodes 15 and 54 are connected to opposite ends of the transformer primary winding, and the "virtual" central reference is established between central electrode 48 and the centre tap of the primary winding, these being connected by an isolating capacitor 62. The differential amplifier 40 is of relatively low gain ($\times 40$) and, since the wanted signals sum and the unwanted pickup signals cancel, the effective gain is doubled ($\times 80$). The instrumentation amplifier 42 is of higher gain ($\times 100$) for a total gain of 8,000 at the output terminals 64, it being supplied with power from a source 64, the connections to the reference electrode 60 being indicated in the conventional manner as respective ground connections.

Figure 8:
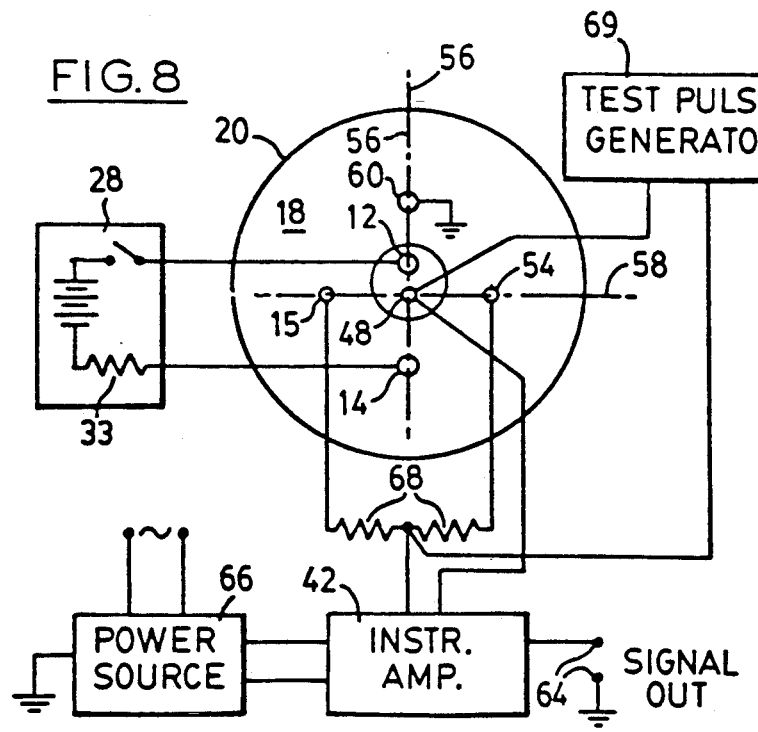
FIG. 8 is a cross-section and schematic circuit diagram, similar to FIG. 7, of a further six-electrode embodiment.

FIG. 8 illustrates an alternative circuit not employing a differential transformer; a pair of series-connected resistors 68 (or a single centre tapped resistor) are connected between the two electrodes 15 and 54, the resistances having a low value relative to the input impedance of the amplifier 42, which is connected between the centre tap of the resistors and the electrode 48. Again a relatively inexpensive instrumentation high gain transformer can be employed instead of a more expensive isolating-type transformer that would otherwise be required.

The separation of the current carrying function of the electrodes from the signal generating function results in substantial practical advantages in the size and type of current power supply that is needed. Specifically it is now found that the supply need only be a single cell or cells of about 1.2 volts, instead of the multiple cell 6 volt heavy duty battery (to supply 60 amps) employed hitherto. The required amp/hour capacity can be provided by connecting a plurality of smaller capacity cells in parallel and this has further substantial advantages that will be described in more detail below.

In order to avoid the noise associated with a rectified AC source the power is supplied from a rechargable storage battery; since this cannot be a perfect source the signal that is measured is lower than the theoretical value by the relation:

$$V_m = V_t(1 - V_s/V_b)$$

where
 $V_m$ = measured signal
 $V_t$ = theoretical signal
 $V_s$ = voltage across signal electrodes, and
 $V_b$ = battery voltage With the 6 volt battery source at 60 amps current the signal voltage between the current carrying electrodes was 0.5 volt, the relation then having the value:

$$V_m = V_t(1 - 0.5/6) = 0.917 V_t$$

so that a correcting factor of 1.09 must be applied to the measured signal values. The energy budget of this apparatus shows a low efficiency of energy use (about 8.3%) in that the signal involves use of only 30 W (0.5 V × 60 A), while the battery must supply 360 W (6 V × 60 A) with the excess dissipated in the ballast resistor, which must be of correspondingly large rating. The voltage across the aperture 22 is however only of the order of 0.12 volt so that $$V_m = V_t(1 - 0.12/60) = 0.98 V_t$$

This is the voltage that is measured by the two non-current carrying electrodes using high input impedance detection circuits, and if the same voltage is obtained from a source of only 1.2 volts the signal amplitude Vm is:

$$V_m = V_t(1 - 0.12/1.2) = 0.9 V_t$$

The signal amplitude is reduced by about 9%, which is tolerable, while the energy budget now has a efficiency of 41.7%, in that the energy at the current carrying electrodes is still 30 W, but the battery need only supply 72 W (60 A × 1.2 V). Nickel cadmium batteries of 10 AH capacity are available and can be used in parallel to provide the full 60 amp current for approximately 90 minutes before recharging is needed, which is possible during the non-sampling periods, so that continuous operation is obtained. The use of a plurality of batteries, plus the use of two or more different values of ballast resistors, permits the provision of a variable test current that can be adjusted to suit the test to be made using relatively simple and inexpensive solid state switches to switch the batteries and resistors in and out of circuit.

Figure 9:
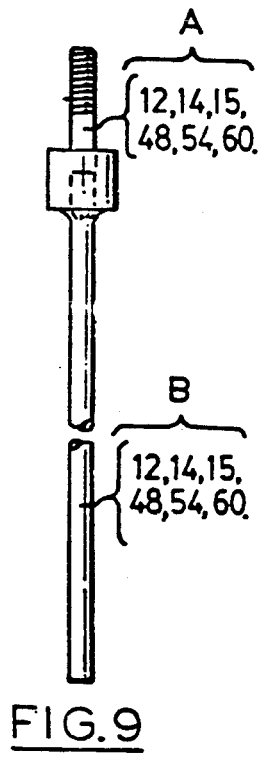
FIG. 9 is a side elevation of an electrode of the apparatus to illustrate a preferred construction thereof.
Figure 10:
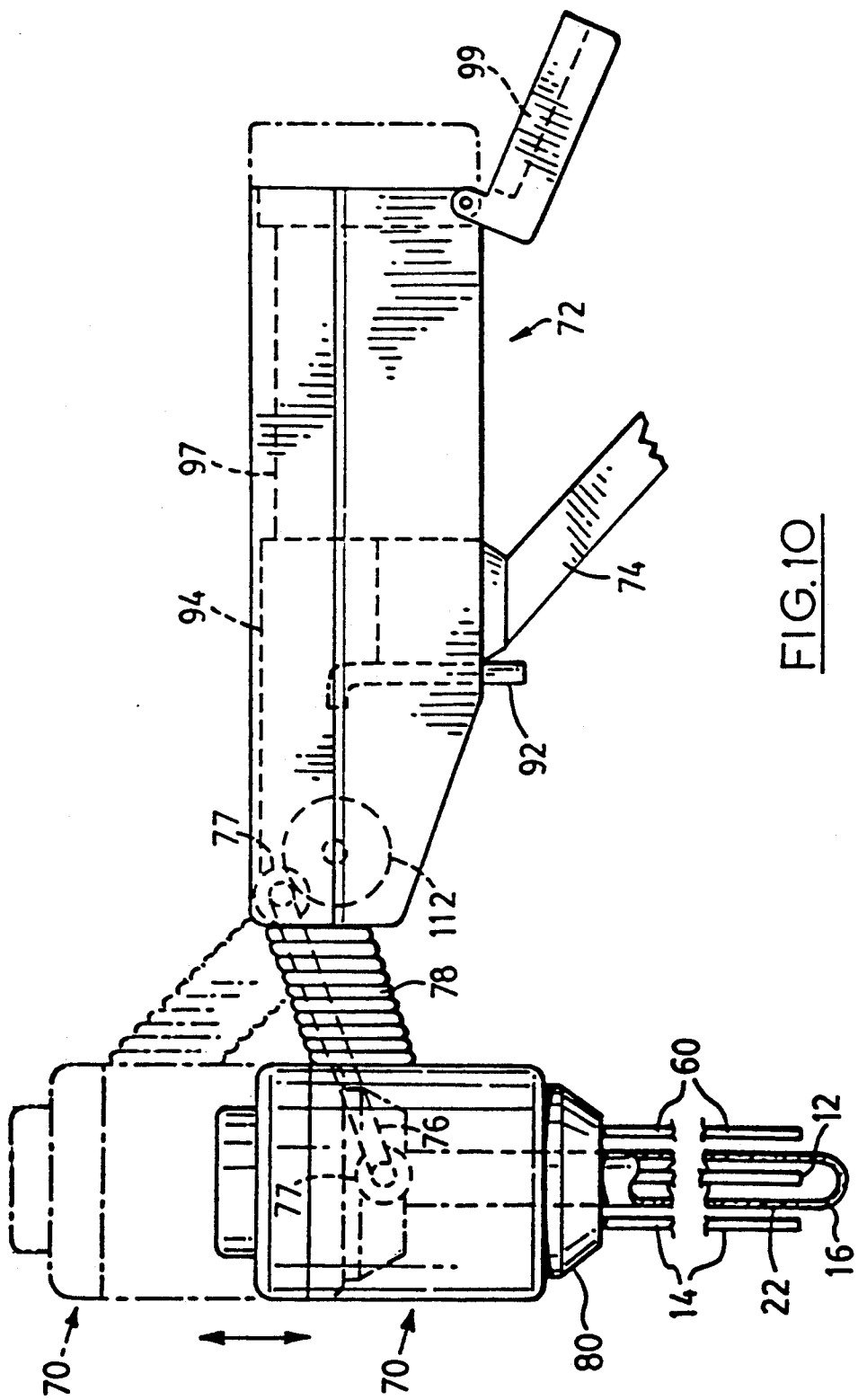
FIG. 10 is a side elevation of a first embodiment of a compact, self contained apparatus comprising separate head and body members.

FIG. 9 illustrates a preferred structure for the electrodes, each of which consists of an immersible portion (given the suffix A) attached to the mounting portion (given the suffix B). The mounting portions must be of a non-corrosive high conductivity metal such as copper or brass, preferably the latter, while the immersible portions are of a high melting point metal able to withstand the repeated immersions in molten aluminum. Most importantly the two different metals employed must have a sufficiently low contact potential at the temperature reached by the junction in use, preferably less than 1 millivolt. As described above, the relatively thin, elongated electrodes can measure up to 90 cms (36 ins) in length, and in operation it is difficult, if not impossible, to prevent them vibrating as they are inserted into and withdrawn from the metal. We have found that the vibration modulates the contact potential generating an A.C. signal that is amplified by the amplifier chain. At gains of more than 2-3,000 the resultant signal produced with contact potentials of about 10 millivolts are about equal in amplitude to the basic noise of the amplifier chain.

We have found that a particularly effective combination is the use of brass for the mounting portion and tungsten for the immersible portion, the two portions being silver soldered together at their junction, such a combination having a contact potential of less than 1 millivolt at 60° C., so that mechanical vibrations produce signals well below the basic noise of the amplifier chain, even at gains as high as 10,000. This is to be compared with the contact potentials of about 30 millivolts obtained at 60° C. with the brass/soft steel electrodes used hitherto. The use of tungsten has the additional benefits that its electrical resistance is relatively low, as compared to soft steel, permitting the use of smaller diameter electrodes, e.g. 6.5 mm (0.25 in) O.D. for the current carrying electrodes, and 2.5 mm (0.10 in) for the other electrodes. Alternatively, if the same diameter electrodes are employed, higher current flows are obtainable since this is limited primarily by the resistance of the electrodes. Tungsten is considerably less soluble in aluminum (7-10 times) than soft steel so that the electrodes have longer life.

For similar reasons of avoidance of spurious signal generation we have found it desirable to firmly anchor all current-carrying wires, even when twisted together as is standard practice, since any mechanical vibration of the wires can produce such signals of sufficient strength to be interfering.

The electrode structures disclosed have a principal object to enable the apparatus to detect with minimum ambiguity relatively small size particles and, as discussed above, this requires primarily that noise and interference be minimized to enable the relatively small wanted signals to be adequately identified. The problem is made difficult by the cubic relationship that exists between particle size and the wanted electric signals. Thus an increase in resolution of 2×, for example to identify particles of 10 microns instead of 20 microns, requires an improvement of 8× in signal strength over the background noise, while an increase to a resolution of 5 microns (4×) requires an improvement of 64×, all while keeping the signal/noise ratio to corresponding values of 2× and 4×. It has also been found that it is possible to reduce substantially the effects of outside interference by suitable physical and electrical design and arrangement of the accompanying circuit elements and their enclosures, particularly by reducing their physical size as much as possible, so that inherently they pick up less random noise. Again, if the circuit elements can be more closely spaced then the electrical connectors are shorter and less liable to pick up interference signals. It has been found in particular that the effects of pick-up of extraneous noise can be substantially reduced by arranging that certain circuit elements are disposed symmetrically about a longitudinal axis which passes through the cluster of electrodes, the axis lying in the plane 56 of the various heads shown in the drawings; if this is done the interference signals produced can be arranged to be in anti-phase relative to one another, so that they tend to cancel one another.

Referring now to FIGS. 10 through 13 the self-contained apparatus comprises two principal parts, namely a head member 70 and a main body member 72, the latter being provided with a mounting member 74 by which it can be mounted in position adjacent the metal containing vessel or transfer runner (not shown) with the cluster of electrodes carried by the head member either inserted in the metal or raised clear thereof. Thus the head member is mounted on the main body member by a pair of transversely spaced arms 76 pivoted at their ends to the two members and enclosed in a flexible neck cover 78, the arms permitting the head member to be moved vertically between a lower operative position shown in solid lines in FIG. 10, in which the electrodes dip into the molten metal, and an upper storage portion shown in broken lines in which the electrodes are clear of the metal surface. The bearings 77 employed to mount these arms are of a type that are resiliently damped to minimize transmission of mechanical vibrations between the two members.

Figure 12:
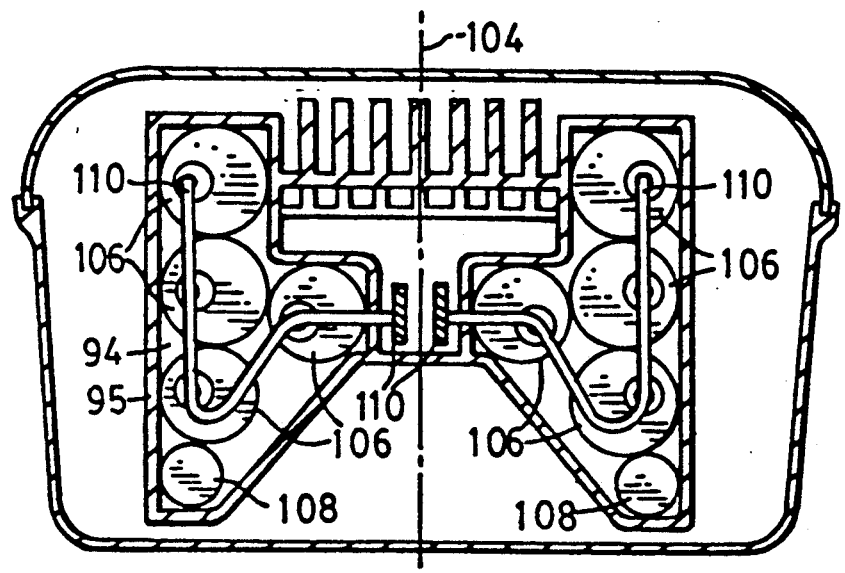
FIG. 12 is a transverse cross-section taken on the line 12—12 of FIG. 11.

The structure of the head member is shown in more detail in the enlarged view of FIG. 12, where the external thin sheet metal covers are shown removed to expose the internal structure. A lower rigid cup like member 80 and an upper rigid cup-like member 82 are connected rigidly together by vertical circumferentially-spaced pillars 84; preferably this structure is of cast aluminum. The lower member 80 mounts the electrode cluster and the sampling tube 16, these extending parallel to one another from its lower side, while a battery-operated preamplifier 86 is mounted immediately above it; the minimum possible of the electronic circuits of the head member is mounted in this location while the greater part, indicated by the block 88, is mounted in the upper cup member 82 where it is more fully protected by the intervening structure against heat from the molten metal. Mechanical items such as the arm bearings 77, and other non-electric items indicated by the block 90, such as pneumatic switches and relays, which are more tolerant of hot environment conditions, are disposed in the space between the two members; additionally this space is supplied with cooled air by means of two cyclone coolers 92 located in the body casing 72 and discharging into the interior of a chamber 94 within the body 72 formed by a metal shielding casing 95. In this embodiment the chamber 94 and casing 95 are T-shape as seen in plan, and are closed off from the remainder of the interior of the body casing, but are open at the foot of the T to the neck 78 and thus to the interior of the head member 70, so that both interiors are supplied with the cooling air. The remainder of the interior of the body member 72 is occupied by circuit boards 97 for the electronics, while the rear end is hinged to the remainder and accomodates computer key board 99.

The tube 16 is made readily replaceable by it extending into a recess in a boss member 96 mounted in an opening in the bottom of the cup member 80, the tube being inserted in and removed from the recess through an annular cuff 98 of resilient material lodged in an annular recess 100. In its fully inserted position the upper edge of the tube engages an O-ring 102. Gas under pressure is then supplied by tube 101 to the gas-tight chamber formed between the cuff and the wall of recess 100, the pressurized gas pressing the cuff tightly into contact with the outer wall of the tube.

Figure 11:
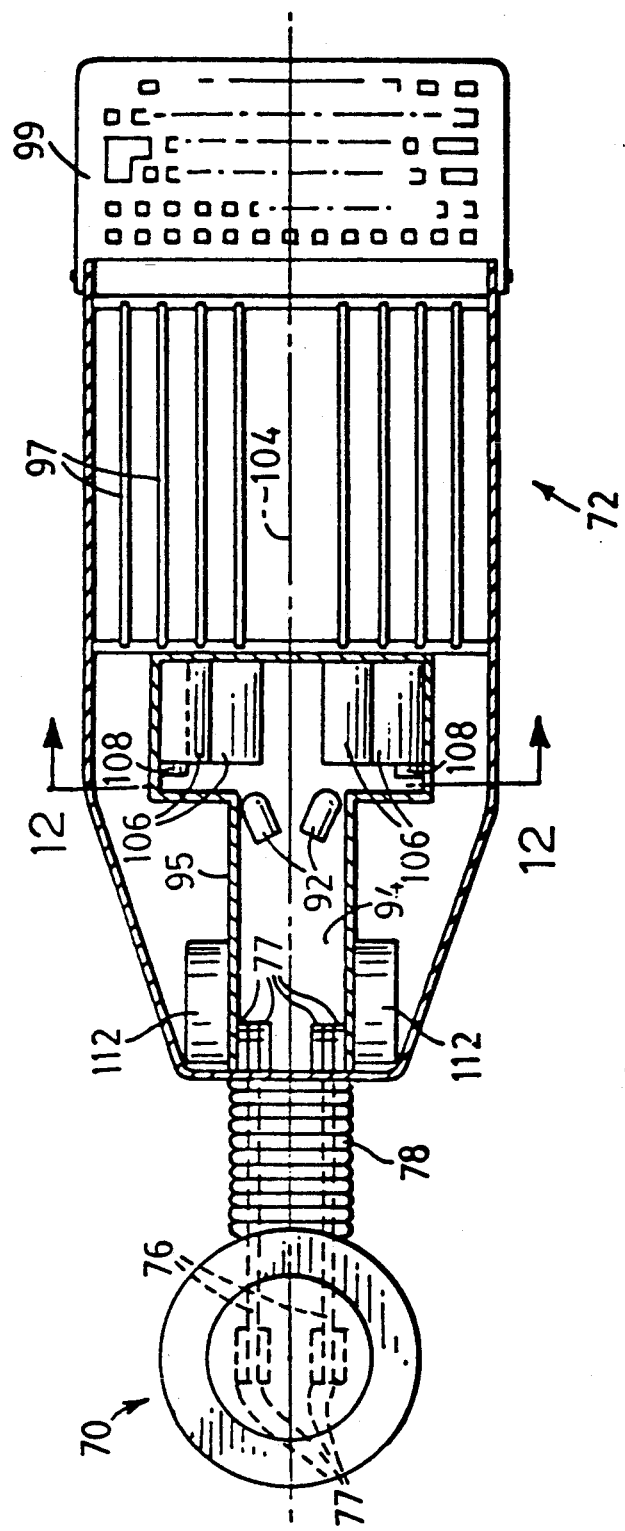
FIG. 11 is a plan view from above of the apparatus of FIG. 10 with a top cover of the body member shown removed.
Figure 13:
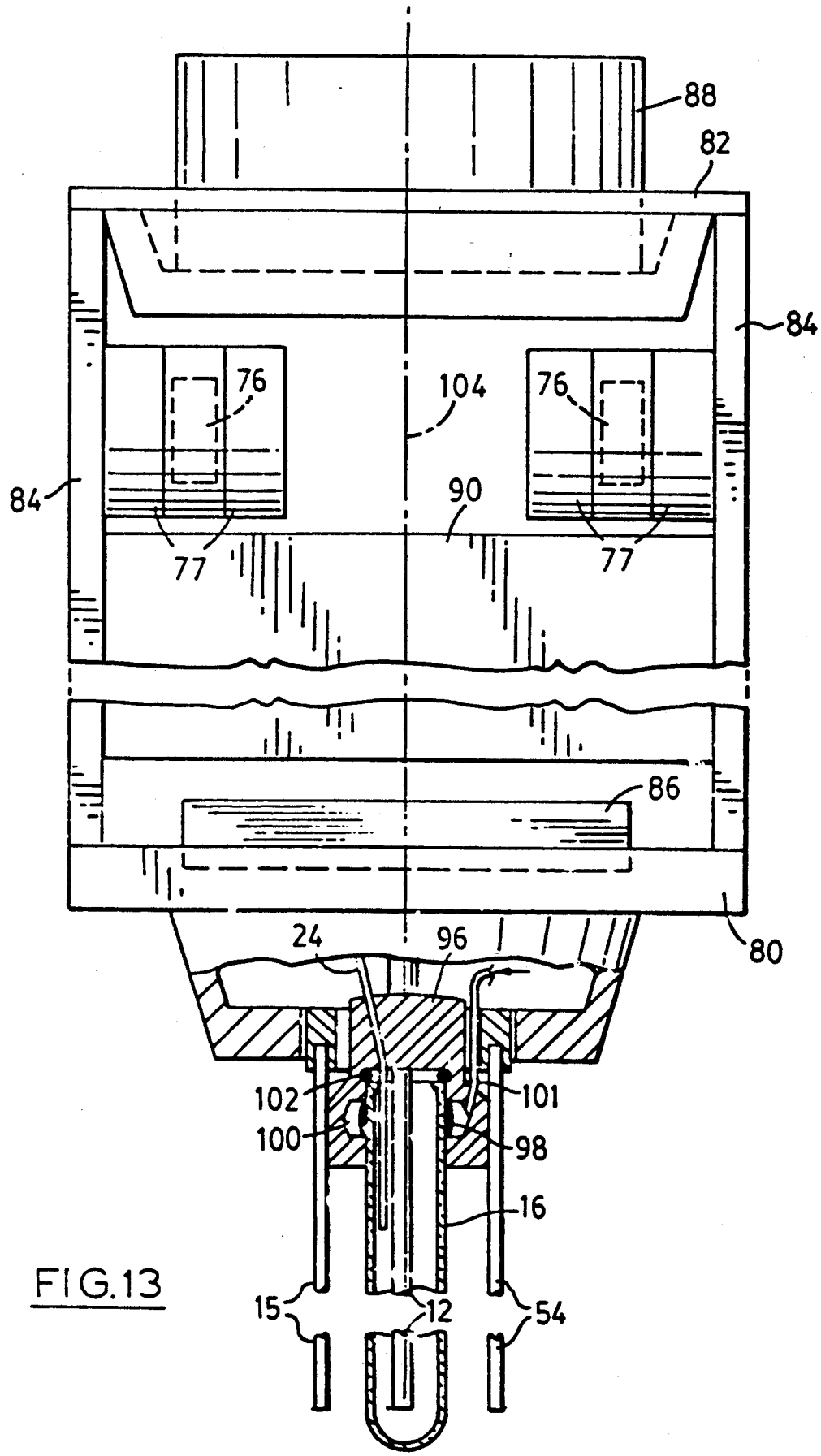
FIG. 13 is an end elevation of the head member of the apparatus of FIGS. 10–12, to a larger scale and with the external covers removed.

The longitudinal axis of symmetry of the apparatus is indicated in FIGS. 11–13 by the reference 104 and it will be noted that it bisects the head member 70, the body member 72 and particularly the T-shaped chamber 94. The cross-bar of the T constitutes a battery compartment containing eight re-chargable batteries 106 that supply the test current and two smaller rechargable batteries 108 that supply the electronic circuits. The batteries 106 are in two mirror-image symmetrical groups of four on opposite sides of plane 104, and the two batteries 108 are also symmetrically disposed with respect to that plane. The batteries are bulky and there is therefore a limit to the closeness of their spacing, so that the current-carrying leads such as common bus connections 110, which act as pick-ups for interference, cannot be shortened below a minimum. With the batteries stacked in this symmetrical manner and connected in circuit with equal numbers from both packs the interference signals picked up by the connections will inherently be of opposite phase and tend to cancel one another. The small amount of non-symmetry caused by the occasional use of one more battery in one pack than in the other is tolerable.

Figure 15:
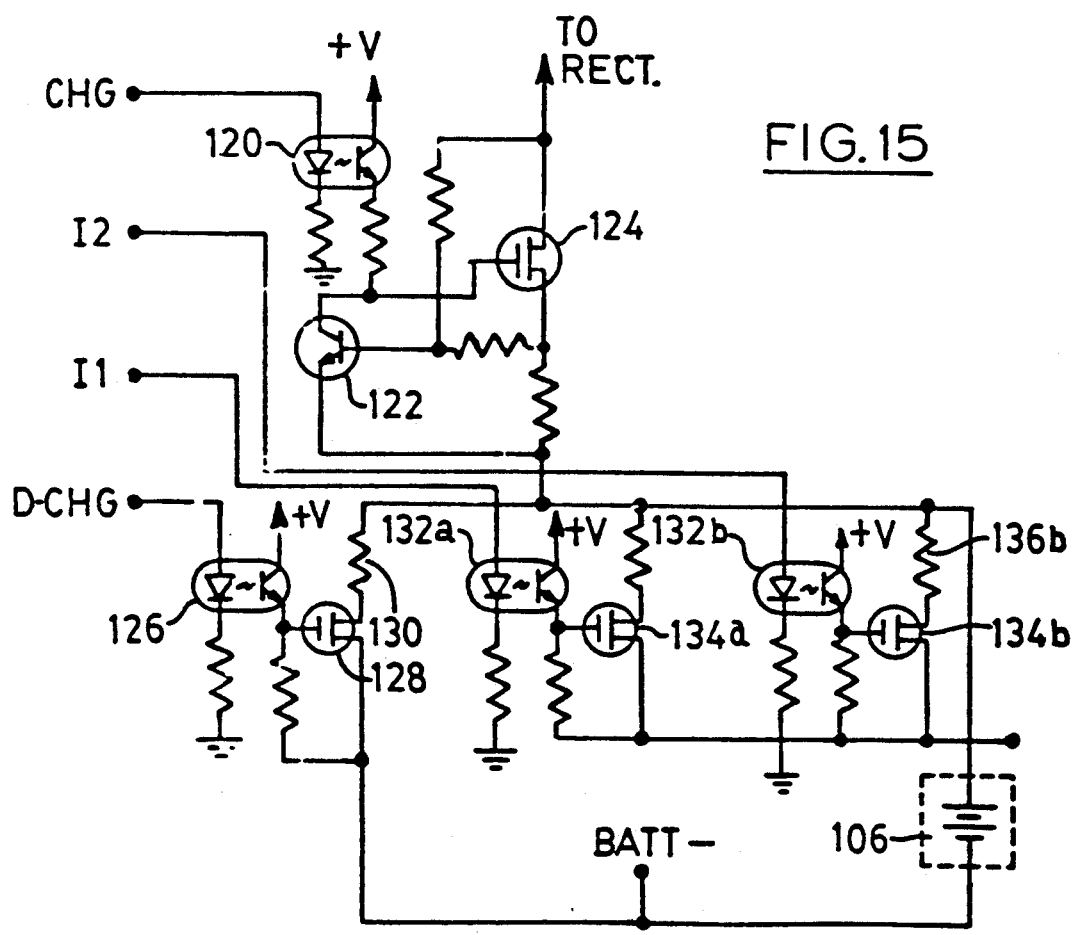
FIG. 15 is a diagram of a battery utilisation and charging circuit for each of the batteries of the apparatus.
Figure 14:
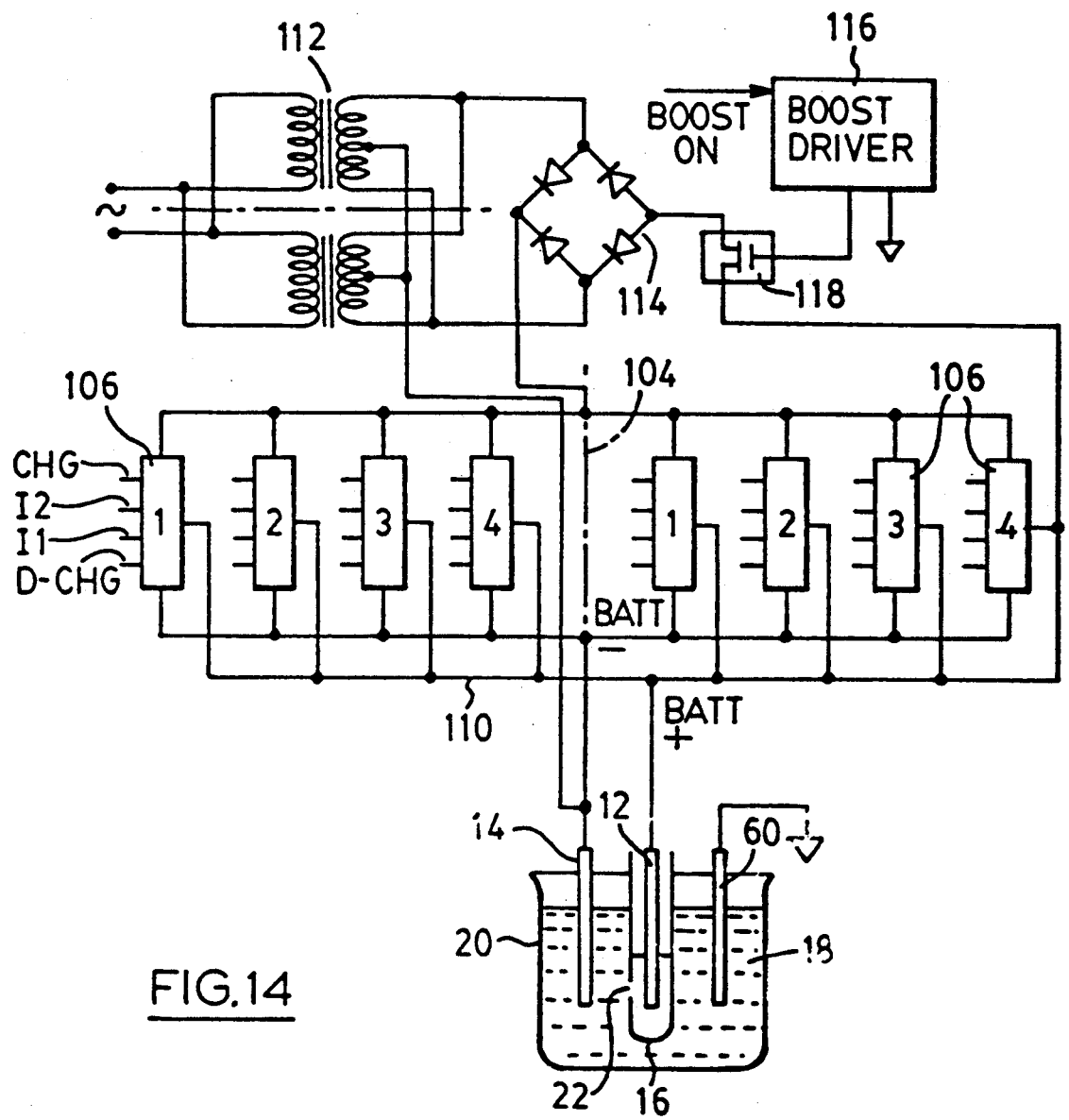
FIG. 14 is a diagram of a battery and boost current circuit for the apparatus of FIGS. 10–13.

FIG. 14 shows a battery and boost current supply portion of the electric circuit, while FIG. 15 shows one of the circuits provided for each of the batteries to control the charging and discharging thereof, and also to control its respective output current by use of different values of ballast resistor. It is found to be advantageous in the operation of this apparatus prior to a test to apply briefly a relatively high boost current across the current carrying electrodes 12 and 14, and it is believed that this acts to clear the aperture 22 of any small debris and gas bubbles that may be adhering to its walls. This current, which may be as high as 300 amps, can be rectified AC and is provided by transformer 112 supplied from an AC source and full-wave rectifier 114, the output of the rectifier being supplied under the control of a boost driver circuit 116 via parallel-connected power mosfets 118 to the two electrodes. The circuit enables the value of the boost current to be controlled, so that it can be adjusted to the minimum value that will give effective clearance of the aperture, such control reducing the possibility of damage to the passage that could be caused by excessive current density in the current path through the passage. The transformer 112 is a particularly large component with a high possibility of interference pick-up and accordingly two equal toroidal coil transformers are used connected in parallel and are disposed mirror symmetrically in the casing on opposite sides of the plane 104, so any such pick-ups are in anti-phase and cancel. This has the incidental advantage that when connected in parallel the AC source can be 110–125 volts, and 220–250 volts when connected in series.

Referring now also to FIG. 15, the opportunity is taken during test periods to recharge the batteries, and this is done by applying a charge control signal at terminal CHG to a respective opto-isolator 120 (e.g. type 4N35), which in turn switches on transistor 122 controlling a power mosfet 124 so that the rectifier 114 is supplying charging current to the respective battery. The battery is connected in circuit to supply current to the electrodes 12 and 14 by applying a respective control signal to terminal D-CHG, and thus to an opto-isolator 126 which controls a power mosfet 128, this portion of the circuit including a ballast resistor 130. The value of the current supplied to the electrodes can be varied, as described above, by connecting different numbers of batteries 106 in parallel, but it can also be varied over an even wider range by applying control signals to either or both of the terminals I1 and I2. Each of these terminals is connected to a respective opto-isolator 132a and 132b controlling a respective power mosfet 134a and 134b and selectively connecting a respective ballast resistor 136a and 136b in the circuit.

This flexibility of control of the batteries can be surprisingly important in obtaining improved resolution. With the prior apparatus a minimum practical size for the bore 22 has been about 300 microns, principally as described above to avoid the possibility that it becomes blocked by any large particles that may happen to be drawn in during the test. Another consideration is that the current density through the passage increases with a squared relation as its size decreases, and can quickly become excessive with the 60 amp supply that is used with that prior apparatus. Assuming for convenience in calculation that all the particles are spherical the value $\Delta V$ of the wanted test signal is given by the relation:

$$\Delta V = \frac{I \cdot 4rd^3}{\pi D^4}$$

where
  I is the test current;
  D is the passage diameter;
  d is the particle diameter; and
  r is the resitivity of the metal.
from which it will be seen that any reduction in passage diameter ($D^4$) is more effective than a corresponding decrease in particle diameter ($d^3$). For example, a one third reduction of the passage size to 200 microns can result in a five-times increase in the test signal, giving the possibility of increased resolution from 10 microns to about 6 microns for the same test signal value. However, a reduction in passage diameter with the same test current results in a squared increase in the current density through the hole, with increased heating and wear, shortening the useful life of the expensive tube, perhaps to the extent that only a few tests can be performed. This is avoided with the apparatus of the invention wherein the controllable battery circuit permits the test current to be set precisely at a suitable value. There is a constantly increasing requirement in the industry for cleaner metal which this invention facilitates by enabling rapid on-line analysis of particle content, and as processes are developed to achieve this the possibility of random large particles being present is reduced, so that smaller apertures, as low as 100 microns, and consequent increased resolution are practical.

Figure 16:
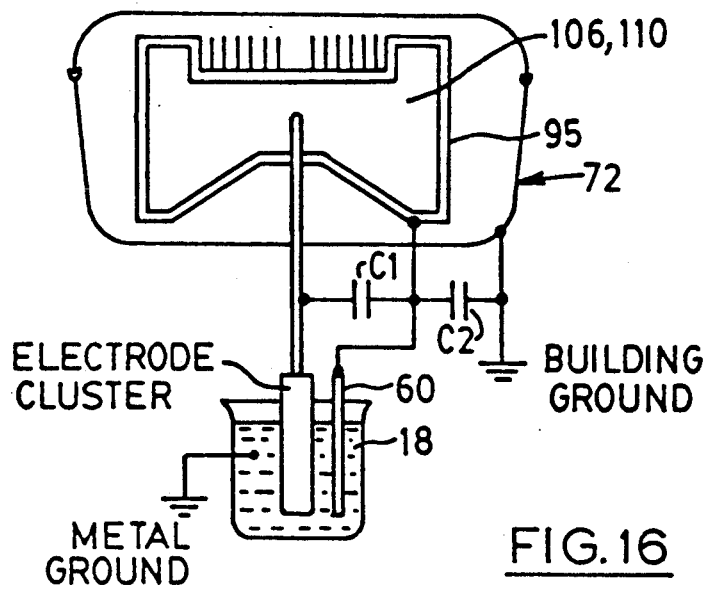
FIG. 16 is a diagram showing an application of a sixth electrode to minimize ground loop current paths.

FIG. 16 illustrates a specific example of the manner in which the additional electrode 60 is employed to reduce spurious currents. Considerations of electrical safety require the use of a building ground connected to the external metal casing 74 and frame of the apparatus, while the metal bath 18 inherently is another ground. The battery pack then acts as one plate of an equivalent capacitor while the casing acts as the other, and different potentials at the two grounds can establish a detrimental current through the capacitor. If, as in this embodiment, the batteries are enclosed in a metal case 95, this case constitutes one plate of an equivalent capacitor C1 while the batteries connected to the electrode cluster constitute the other plate. The case 95 constitutes an intermediate shield between the batteries and also acts as a plate of a second equivalent capacitor C2 connected in series with the capacitor C1, the external casing 72 being the other plate of C2. The shield is connected by a heavy wire to the electrode 60, which is also of relatively large diameter (e.g. 12.5 mm). Any undesirable currents created by different ground potentials circulate harmlessly in C1, but none can circulate in C2 since both plates are at the same ground potential. The use of such an additional electrode obviates the need for bulky and expensive isolation transformers. Again, the common sides of all D.C. supplies that are line-derived should be tied to this electrode by a separate heavy wire to divert spurious AC currents that are injected by the inherent capacitance of the associated input transformers.

Figure 17:
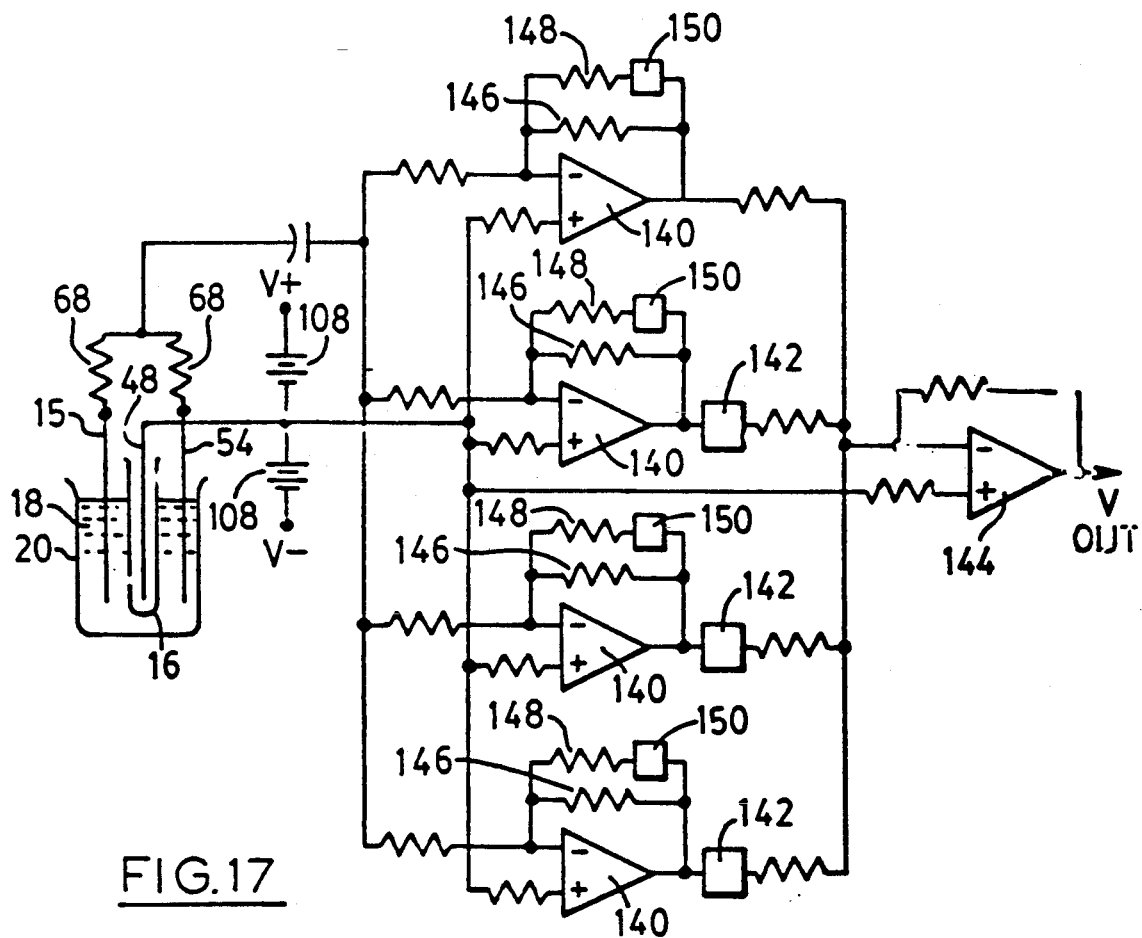
FIG. 17 is a cicuit diagram of a reduced-noise multiple test signal amplifier arrangement for the apparatus.

FIG. 17 illustrates a preferred form of an amplifier circuit to obtain the necessary high gain while establishing the lowest possible total system noise level; for example this should not be more than 0.5 microvolts (including amplifier noise) to be able to detect particulates of 10 microns diameter moving through a passage of 300 microns diameter using a current of 60 amps and with a signal/noise ratio of not less than 4. Instrumentation amplifiers with a gain as high as is required ($\times 10,000$) have high intrinsic noise and are limited in bandwith. The achievement of high gain with sufficiently low noise level has the advantage that it is then possible to reduce the value of the test current required for satisfactory signals to be obtained, with a consequent reduced load on the batteries. A more satisfactory amplifier circuit shown in the figure employs a plurality (four in this embodiment) of small bandwidth operational amplifiers of low enough noise figure (1.1 nanovolts) connected in parallel with their outputs feeding to a unity gain amplifier, this permitting sufficient bandwith (20 KHz) to be obtained with a lower total noise. It now also becomes possible to obtain variable gain by switching amplifiers in and out of circuit and also by the provision of additional feedback resistors that can be switched in and out of circuit; this is particularly useful if the signal is found to be too strong as the result of the presence of large particulates, when the gain can readily be reduced to a suitable value.

The circuit comprises four amplifiers 140 (e.g. type LT 1028 of Linear Technology) connected in parallel with one amplifier permanently connected, while the other three are selectively connectable by electronic switches 150. The amplifiers are supplied with power from the two separate batteries 108, which reduces ground loop current problems. The wanted test signal is in phase in all four amplifiers and their sum has a linear relationship, namely:

$$V_{out} = 4 \times V_{in}$$

Since amplifier noise is random their sum is the square root of the sum of their squares so that $$V_{total\ noise} = 2 \times V_{single\ amplifier\ noise}$$

to give a 2 times improvement in signal/noise ratio; at the low signal levels involved this constitutes a substantial and worthwhile improvement.

Figure 18:
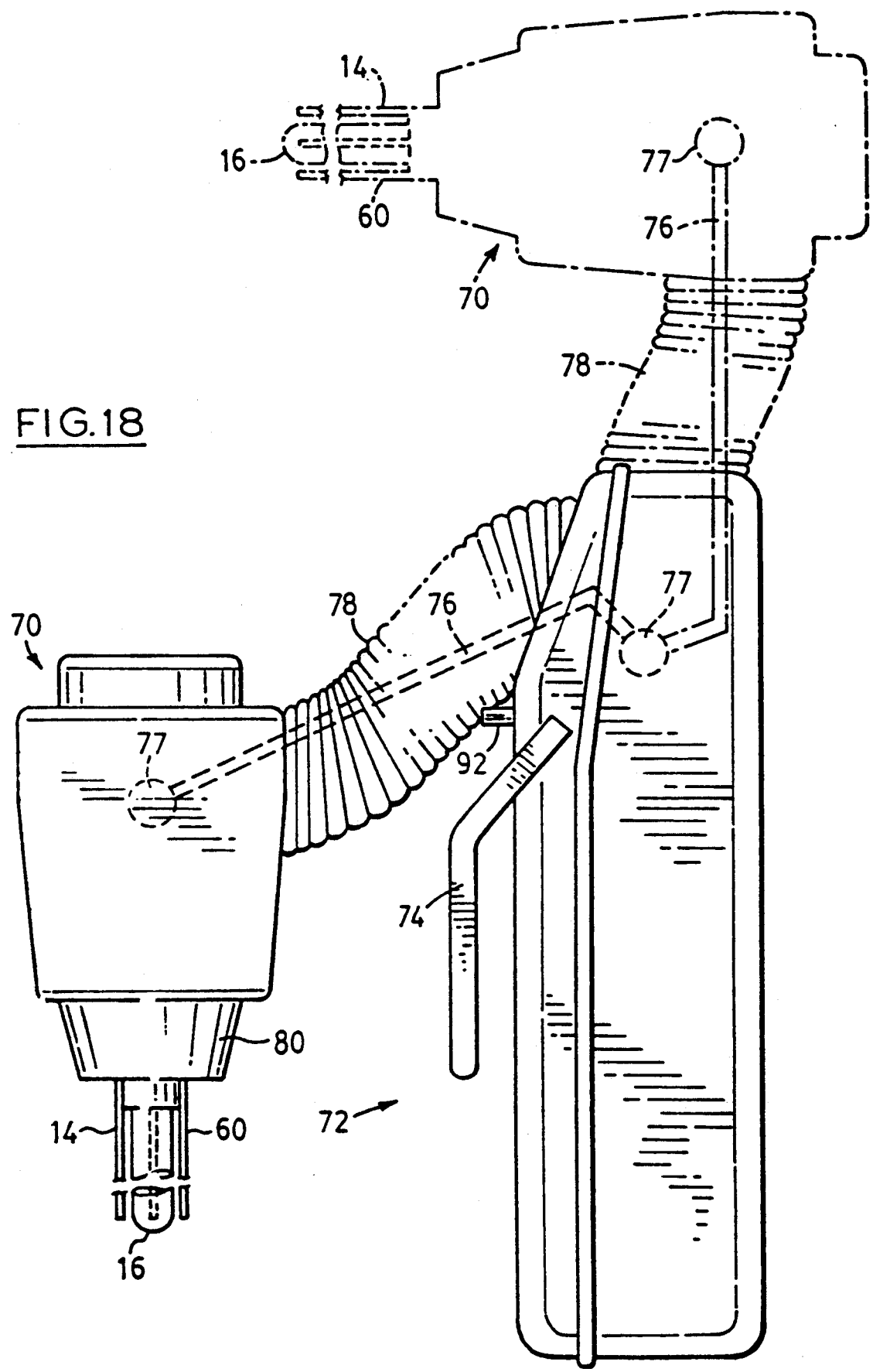
FIG. 18 is a side elevation of another structure for a self-contained apparatus employing separate head and body members.

FIG. 18 shows in side elevation another physical structure for a self-contained apparatus, the same references being used for similar parts wherever that is possible. The apparatus is intended for use with the longitudinal dimension of the body part 72 vertical so that it can be used in locations where the horizontally-extending body of the embodiment of FIGS. 10 and 11 might cause some obstruction; the computer keyboard is now provided as a separate unit which is not shown. The shape and arrangement of the arms 76 is made such that the head portion can be moved from an operative position in which it is parallel to and alongside the body 72 to a stored or access position in which it is disposed vertically above the body to be well clear of the metal and somewhat more accessible to an operator.

We claim:

1. Apparatus for the detection and measurement of particles in liquid metal comprising:
   an electrically insulating wall having a passage therein for the passage of molten metal therethrough;
   means for passing molten metal through the passage in the form of a stream thereof;
   a pair of current supply electrodes disposed on opposite sides of the wall for insertion into the liquid metal to establish between the electrodes a current path through the passage;
   a pair of current supply leads connected respectively to the current supply electrodes for passing a current in the current path from a source thereof;
   at least a third electrode for insertion into the liquid metal with the first-mentioned pair of electrodes;
   a pair of test leads connected to a pair of the electrodes on opposite sides of the wall for connection to detection means for detecting the voltage difference between the pair of electrodes resulting from the current and for detecting changes in the voltage difference resulting from the passage of differently-conducting particles through the passage and for the consequent production of a corresponding test signal;
   the last-mentioned pair of the electrodes constituting at least part of an interference antenna producing an interference signal from incident electric or magnetic interference, which interference signal is superimposed on the test signal;
   another pair of the three electrodes constituting a cancellation antenna disposed adjacent the said interference antenna to produce an interference cancellation signal from the said incident interference;
   and means for adding the interference cancellation signal to the said test signal in opposition to the interference signal to reduce the amplitude of the interference signal.

2. Apparatus as claimed in claim 1, wherein the two current supply electrodes and the third electrode lie in the same plane.

3. Apparatus as claimed in claim 1, and including a fourth electrode for insertion into the liquid metal and measuring means connected between the fourth electrode and one of the first-mentioned three electrodes disposed on the opposite side of the wall from the fourth electrode for determination of the size of the passage by determination of the voltage difference therethrough produced by the current in the current path.

4. Apparatus as claimed in claim 3, and including a further electrode for insertion into the liquid metal, and means connecting the further electrode in the apparatus to connect the apparatus to the liquid metal as a ground.

5. Apparatus as claimed in claim 3, wherein the said test and interference signals are fed to a differential amplifier as one input thereof, and the said interference cancellation signal is fed to the differential amplifier as another input thereof, the output of the amplifier being the difference between the two inputs.

6. Apparatus as claimed in claim 1, and including a fourth electrode for insertion into the liquid metal, disposed on the opposite side of the wall means to the said third electrode, and measuring means connected between the third and fourth electrodes for determination of the size of the passage by determination of the voltage difference therethrough produced by the current in the current path.

7. Apparatus as claimed in claim 1, and including a fourth and a fifth electrode for insertion into the liquid metal, wherein a first pair of the electrodes constitute the interference antenna, a second pair of the electrodes having one of the electrodes of the first pair in common constitute the cancellation antenna, and a third pair of the electrodes disposed on opposite sides of the wall means have means connected therebetween for determination of the size of the passage by determination of the voltage difference therethrough produced by the current in the current path.

8. Apparatus as claimed in claim 7, and including a further electrode for insertion into the liquid metal, and means connecting the further electrode in the apparatus to connect the apparatus to the liquid metal as a ground.

9. Apparatus as claimed in claim 7 wherein the said test and interference signals are fed to a differential amplifier as one input thereof, and the said interference cancellation signal is fed to the differential amplifier as another input thereof, the output of the amplifier being the difference between the two inputs.

10. Apparatus as claimed in claim 1, and including a further electrode for insertion into the liquid metal, and means connecting the further electrode in the apparatus to connect the apparatus to the liquid metal as a ground.

11. Apparatus as claimed in claim 1, wherein the said test and interference signals are fed to a differential amplifier as one input thereof, and the said interference cancellation signal is fed to the differential amplifier as another input thereof, the output of the amplifier being the difference between the two inputs.

12. Apparatus as claimed in claim 1, wherein the said test and interference signals are fed to the opposite ends of a centre tapped impedance, the centre tap of which constitutes an output terminal, the resultant output being supplied to an amplifier or to a plurality of parallel connected amplifiers.

13. Apparatus as claimed in claim 1, wherein a test pulse generator is connected between the two electrodes between which a test signal is produced and is adapted to generate simulated test pulses for examination of the response of the apparatus.

14. Apparatus as claimed in claim 1, wherein an apparatus body mounting the electrically insulating wall and the electrodes is symmetrical about a longitudinal plane, and a power supply for the apparatus is in two mirror symmetrical portions disposed on opposite sides of the longitudinal plane.

15. Apparatus as claimed in claim 14, wherein the power supply comprises a plurality of independently selectable separate batteries and a transformer, both of which are in two mirror symmetrical portions disposed on opposite sides of the longitudinal plane.

16. Apparatus as claimed in claim 1, and comprising a head member mounting the electrically insulating wall and the electrodes;
  a body member mounting a power supply for the apparatus; and
  an arm mounting the head member for movement relative to the body member between an operative position in which the electrodes are insertable in the molten metal and a storage position in which they are spaced from the molten metal.

17. Apparatus as claimed in claim 16,
  wherein the head member, and the body member are symmetrical about a longitudinal plane, and the power supply for the apparatus is in two mirror symmetrical portions disposed on opposite sides of the longitudinal plane.

18. Apparatus as claimed in claim 1, and comprising a head member mounting the electrically insulating wall and the electrodes; and
  a body member mounting a power supply for the apparatus;
  wherein the head member has the electrodes mounted at its lower end;
  a head amplifier connected to the pair of test leads is mounted immediately above the electrodes;
  non-electric elements of the apparatus are mounted above the head amplifier; and
  an amplifier connected to the head amplifier is mounted above the non-electric elements.

19. Apparatus as claimed in claim 1, wherein each electrode comprises an immersible portion of tungsten and a mounting portion having a contact potential of less than 1 millivolt with tungsten at the temperature of operation.

20. Apparatus as claimed in claim 1, wherein the insulating wall comprises a tube, and means for mounting the tube in the apparatus comprise a resilient cuff through which the tube passes, the cuff being pressurized to grip the tube and hold it in the apparatus.

21. Apparatus for the detection and measurement of particles in liquid metal comprising:
  an electrically insulating wall having a passage therein for the passage of molten metal therethrough;
  means for passing molten metal through the passage in the form of a stream thereof;
  a pair of current supply electrodes disposed on opposite sides of the wall for insertion into the liquid metal to establish between the electrodes a current path through the passage;
  a pair of current supply leads connected respectively to the current supply electrodes for passing a current in the current path from a source thereof;
  a third, fourth and fifth electrodes for insertion into the liquid metal with the pair of current supply electrodes so that one of the said third, fourth and fifth electrodes is disposed on an opposite side of the wall from the other two electrodes;
  a pair of test leads connected to a pair of the third, fourth and fifth electrodes which are on opposite sides of the wall for connection to measuring means for detecting the voltage difference between those electrodes resulting from the electric field and for detecting changes in the voltage difference resulting from the passage of differently-conducting particles through the passage and for the consequent production of a corresponding test signal;
  measuring means connected to the test leads to receive the test signal that is thereby produced;
  the last-mentioned pair of the electrodes constituting at least part of an interference antenna producing an interference signal from incident electric or magnetic interference, which interference signal is superimposed on the test signal;
  another pair of the third, fourth and fifth electrodes constituting a cancellation antenna disposed adjacent the said interference antenna to produce an interference cancellation signal from the said interference; and
  means for adding the interference cancellation signal to the said test signal in opposition to the interference signal to reduce the amplitude of the interference signal.

22. Apparatus as claimed in claim 21, wherein the third, fourth and fifth electrodes are so disposed relative to one another that the planes of the interference and cancellation antennae are parallel and are at right angles to the plane of the pair of current supply electrodes.

23. Apparatus as claimed in claim 22, including measuring means connected between a pair of the third, fourth and fifth electrodes disposed on opposite sides of the wall from one another for determination of the size of the passage by determination of the voltage difference therethrough produced by the electric field.

24. Apparatus as claimed in claim 21, including measuring means connected between a pair of the third, fourth and fifth electrodes disposed on opposite sides of the wall from one another for determination of the size of the passage by determination of the voltage difference therethrough produced by the electric field.

25. Apparatus as claimed in claim 21, and including a further electrode for insertion into the liquid metal, and means connecting the further electrode in the apparatus to connect the apparatus to the liquid metal as a ground.

26. Apparatus as claimed in claim 21, wherein the said test and interference signals are fed to a differential amplifier as one input thereof, and the said interference cancellation signal is fed to the differential amplifier as another input thereof, the output of the amplifier being the difference between the two inputs.

27. Apparatus as claimed in claim 21, wherein the said test and interference signals are fed to the opposite ends of a centre tapped impedance, the centre tap of which constitutes an output terminal, the resultant output being supplied to an amplifier or to a plurality of parallel connected amplifiers.

28. Apparatus as claimed in claim 21, wherein a test pulse generator is connected between the two electrodes between which a test signal is produced and is adapted to generate simulated test pulses for examination of the response of the apparatus.

29. Apparatus as claimed in claim 21, wherein an apparatus body mounting the electrically insulating wall and the electrodes is symmetrical about a longitudinal plane, and a power supply for the apparatus is in two mirror symmetrical portions disposed on opposite sides of the longitudinal plane.

30. Apparatus as claimed in claim 29, wherein the power supply for the apparatus comprises a plurality of independently selectable separate batteries and a transformer, both of which are in two mirror symmetrical portions disposed on opposite sides of the longitudinal plane.

31. Apparatus as claimed in claim 21, and comprising a head member mounting the electrically insulating wall and the electrodes;
- a body member mounting a power supply for the apparatus; and
- an arm mounting the head member for movement relative to the body member between an operative position in which the electrodes are insertable in the molten metal and a storage position in which they are spaced from the molten metal.

32. Apparatus as claimed in claim 31,
- wherein the head member, and the body member are symmetrical about a longitudinal plane, and the power supply for the apparatus is in two mirror symmetrical portions disposed on opposite sides of the longitudinal plane.

33. Apparatus as claimed in claim 21, and comprising a head member mounting the electrically insulating wall and the electrodes; and
- a body member mounting a power supply for the apparatus;
- wherein the head member has the electrodes mounted at its lower end;
- a head amplifier connected to the pair of test leads is mounted immediately above the electrodes;
- non-electric elements of the apparatus are mounted above the head amplifier; and
- an amplifier connected to the head amplifier is mounted above the non-electric elements.

34. Apparatus as claimed in claim 21, wherein each electrode comprises an immersible portion of tungsten and a mounting portion having a contact potential of less than 1 millivolt with tungsten at the temperature of operation.

35. Apparatus as claimed in claim 21, wherein the insulating wall comprises a tube, and means for mounting the tube in the apparatus comprise a resilient cuff through which the tube passes, the cuff being pressurized to grip the tube and hold it in the apparatus.

* * * * *